United States Patent
Medoff et al.

(10) Patent No.: US 7,074,918 B2
(45) Date of Patent: Jul. 11, 2006

(54) CELLULOSIC AND LIGNOCELLULOSIC MATERIALS AND COMPOSITIONS AND COMPOSITES MADE THEREFROM

(75) Inventors: Marshall Medoff, Brookline, MA (US); Arthur P. Lagace, Newtonville, MA (US)

(73) Assignee: Xyleco, Inc., Brookline, MA (US)

( * ) Notice: Subject to any disclaimer, the term of this patent is extended or adjusted under 35 U.S.C. 154(b) by 28 days.

(21) Appl. No.: 10/615,748

(22) Filed: Jul. 9, 2003

(65) Prior Publication Data

US 2005/0080168 A1    Apr. 14, 2005

Related U.S. Application Data

(60) Division of application No. 09/772,593, filed on Jan. 30, 2001, which is a continuation-in-part of application No. 09/337,580, filed on Jun. 22, 1999, now Pat. No. 6,207,729, which is a continuation-in-part of application No. 09/338,209, filed on Jun. 22, 1999, now abandoned, which is a continuation-in-part of application No. 09/290,031, filed on Apr. 9, 1999, now Pat. No. 6,258,876, which is a continuation-in-part of application No. 08/961,863, filed on Oct. 31, 1997, now Pat. No. 5,973,035, which is a continuation-in-part of application No. 08/921,807, filed on Sep. 2, 1997, now Pat. No. 5,952,105.

(51) Int. Cl.
*B32B 21/10* (2006.01)
*C08B 1/00* (2006.01)
*D04H 1/00* (2006.01)

(52) U.S. Cl. .................. 536/56; 428/292.1; 428/292.4

(58) Field of Classification Search .................. 536/54, 536/30, 56; 424/292.1, 292.4
See application file for complete search history.

(56) References Cited

U.S. PATENT DOCUMENTS

| | | |
|---|---|---|
| 1,824,221 A | 9/1931 | Mason |
| 2,516,847 A | 8/1950 | Boehm |
| 2,519,442 A | 8/1950 | Delorme et al. |
| 2,558,378 A | 6/1951 | Petry |
| 2,635,976 A | 4/1953 | Meiler et al. |
| 2,658,828 A | 11/1953 | Pattilloch |
| 2,665,261 A | 1/1954 | Baker |
| 2,680,102 A | 6/1954 | Becher |
| 2,757,150 A | 7/1956 | Heritage |
| 2,789,903 A | 4/1957 | Lukman et al. |
| 2,935,763 A | 5/1960 | Newman et al. |
| 3,308,218 A | 3/1967 | Wiegand et al. |
| 3,309,444 A | 3/1967 | Schueler |
| 3,493,527 A | 2/1970 | Schueler |
| 3,516,953 A | 6/1970 | Wood |
| 3,645,939 A | 2/1972 | Gaylord |
| 3,671,615 A | 6/1972 | Price |
| 3,697,364 A | 10/1972 | Boustany |
| 3,709,845 A | 1/1973 | Boustany |
| 3,718,536 A | 2/1973 | Downs et al. |
| 3,836,412 A | 9/1974 | Boustany et al. |
| 3,878,143 A | 4/1975 | Baumann et al. |
| 3,888,810 A | 6/1975 | Shinomura |
| 3,943,079 A | 3/1976 | Hamed |
| 3,956,541 A | 5/1976 | Pringle |
| 3,956,555 A | 5/1976 | McKean |
| 4,005,162 A | 1/1977 | Bucking |
| 4,016,232 A | 4/1977 | Pringle |
| 4,020,212 A | 4/1977 | Erickson |
| 4,033,913 A | 7/1977 | Sunden |
| 4,045,603 A | 8/1977 | Smith |
| 4,056,591 A | 11/1977 | Goettler et al. |
| 4,058,580 A | 11/1977 | Flanders |
| 4,097,648 A | 6/1978 | Pringle |
| 4,112,038 A | 9/1978 | Garner |
| 4,113,908 A | 9/1978 | Shinomura |
| 4,115,497 A | 9/1978 | Halmo et al. |
| 4,145,389 A | 3/1979 | Smith |
| 4,168,251 A | 9/1979 | Schinzel et al. |
| 4,187,352 A | 2/1980 | Klobbie |
| 4,188,259 A | 2/1980 | Mamers et al. |
| 4,203,876 A | 5/1980 | Dereppe et al. |
| 4,204,010 A | 5/1980 | Kramm et al. |
| 4,228,116 A | 10/1980 | Colombo et al. |
| 4,239,679 A | 12/1980 | Rolls et al. |
| 4,244,847 A | 1/1981 | Posiviata et al. |
| 4,244,903 A | 1/1981 | Schnause |
| 4,248,743 A | 2/1981 | Goettler |
| 4,248,820 A | 2/1981 | Haataja |
| 4,250,222 A | 2/1981 | Mavel et al. |
| 4,263,184 A | 4/1981 | Leo et al. |
| 4,265,846 A | 5/1981 | Shen et al. |
| 4,273,688 A | 6/1981 | Porzel et al. |
| 4,277,428 A | 7/1981 | Luck et al. |
| 4,279,790 A | 7/1981 | Nakajima |
| 4,281,039 A | 7/1981 | Miura et al. |
| 4,290,988 A | 9/1981 | Nopper et al. |

(Continued)

FOREIGN PATENT DOCUMENTS

AU    47811/90    1/1989

(Continued)

OTHER PUBLICATIONS

Abstract of JP 09267441, filed Oct. 14, 1997, in Chemical Abstracts 127:294599.

(Continued)

*Primary Examiner*—Elli Peselev
(74) *Attorney, Agent, or Firm*—Fish & Richardson P.C.

(57) ABSTRACT

Cellulosic or lignocellulosic materials, and compositions and composites made therefrom, are disclosed.

9 Claims, 1 Drawing Sheet

U.S. PATENT DOCUMENTS

| | | |
|---|---|---|
| 4,303,019 A | 12/1981 | Haataja et al. |
| 4,305,901 A | 12/1981 | Prince et al. |
| 4,311,554 A | 1/1982 | Herr |
| 4,311,621 A | 1/1982 | Nishizawa et al. |
| 4,318,351 A | 3/1982 | Munk |
| 4,323,625 A | 4/1982 | Coran et al. |
| 4,328,136 A | 5/1982 | Blount |
| 4,376,144 A | 3/1983 | Goettler |
| 4,382,108 A | 5/1983 | Carroll et al. |
| 4,393,020 A | 7/1983 | Li et al. |
| 4,414,267 A | 11/1983 | Coran et al. |
| 4,420,351 A | 12/1983 | Lussi et al. |
| 4,426,470 A | 1/1984 | Wessling et al. |
| 4,440,708 A | 4/1984 | Haataja et al. |
| 4,454,091 A | 6/1984 | Chion et al. |
| 4,455,709 A | 6/1984 | Zanini |
| 4,481,701 A | 11/1984 | Hewitt |
| 4,491,553 A | 1/1985 | Yamada et al. |
| 4,503,115 A | 3/1985 | Hemels et al. |
| 4,505,869 A | 3/1985 | Nishibori |
| 4,506,037 A | 3/1985 | Suzuki et al. |
| 4,508,595 A | 4/1985 | Gasland |
| 4,551,294 A | 11/1985 | Wottka et al. |
| 4,559,376 A | 12/1985 | Kubat |
| 4,562,218 A | 12/1985 | Fornadel et al. |
| 4,594,372 A | 6/1986 | Natov et al. |
| 4,597,928 A | 7/1986 | Terentiev et al. |
| 4,608,922 A | 9/1986 | Pohl |
| 4,610,900 A | 9/1986 | Nishibori |
| 4,624,890 A | 11/1986 | Lloyd et al. |
| 4,632,170 A | 12/1986 | Pohl |
| 4,645,631 A | 2/1987 | Hegenstaller et al. |
| 4,659,754 A | 4/1987 | Edwards et al. |
| 4,663,225 A | 5/1987 | Farley et al. |
| 4,674,414 A | 6/1987 | Nülle et al. |
| 4,686,251 A | 8/1987 | Ostermann et al. |
| 4,687,793 A | 8/1987 | Motegi et al. |
| 4,716,062 A | 12/1987 | Klein |
| 4,717,742 A | 1/1988 | Beshay |
| 4,734,236 A | 3/1988 | Davis |
| 4,737,532 A | 4/1988 | Fujita et al. |
| 4,738,723 A | 4/1988 | Frizzell et al. |
| 4,746,688 A | 5/1988 | Bistak et al. |
| 4,769,109 A | 9/1988 | Tellvik et al. |
| 4,769,274 A | 9/1988 | Tellvik et al. |
| 4,791,020 A | 12/1988 | Kokta |
| 4,810,445 A | 3/1989 | Lamb, Sr. et al. |
| 4,818,604 A | 4/1989 | Tock |
| 4,833,181 A | 5/1989 | Narukawa et al. |
| 4,851,458 A | 7/1989 | Hopperdietzel |
| 4,865,788 A | 9/1989 | Davis |
| 4,874,095 A | 10/1989 | Warych |
| 4,894,192 A | 1/1990 | Warych |
| 4,911,700 A | 3/1990 | Makoui et al. |
| 4,915,764 A | 4/1990 | Miani |
| 4,927,579 A | 5/1990 | Moore |
| 4,929,498 A | 5/1990 | Suskind et al. |
| 4,935,182 A | 6/1990 | Ehner et al. |
| 4,960,548 A | 10/1990 | Ikeda et al. |
| 4,963,603 A | 10/1990 | Felegi, Jr. et al. |
| 4,968,463 A | 11/1990 | Levasseur |
| 4,973,440 A | 11/1990 | Tamura et al. |
| 4,978,489 A | 12/1990 | Radvan et al. |
| 4,988,478 A | 1/1991 | Held |
| 5,002,713 A | 3/1991 | Palardy et al. |
| 5,008,310 A | 4/1991 | Beshay |
| 5,009,586 A | 4/1991 | Pallmann |
| 5,028,266 A | 7/1991 | Rettenmaier |
| 5,057,167 A | 10/1991 | Gersbeck |
| 5,064,692 A | 11/1991 | Hofmann et al. |
| 5,075,057 A | 12/1991 | Hoedl |
| 5,075,359 A | 12/1991 | Castagna et al. |
| 5,082,605 A | 1/1992 | Brooks et al. |
| 5,084,135 A | 1/1992 | Brooks et al. |
| 5,087,400 A | 2/1992 | Theuveny |
| 5,088,910 A | 2/1992 | Goforth et al. |
| 5,093,058 A | 3/1992 | Harmon et al. |
| 5,096,046 A | 3/1992 | Goforth et al. |
| 5,096,406 A | 3/1992 | Brooks et al. |
| 5,100,545 A | 3/1992 | Brooks |
| 5,100,603 A | 3/1992 | Neefe |
| 5,104,411 A | 4/1992 | Makoui et al. |
| 5,120,776 A | 6/1992 | Raj et al. |
| 5,124,519 A | 6/1992 | Roy et al. |
| 5,134,023 A | 7/1992 | Hsu |
| 5,137,668 A | 8/1992 | Lamb, Sr. |
| 5,155,147 A | 10/1992 | Dietz et al. |
| 5,183,837 A | 2/1993 | Lepori et al. |
| 5,194,461 A | 3/1993 | Bergquist et al. |
| 5,213,021 A | 5/1993 | Goforth et al. |
| 5,254,617 A | 10/1993 | Inoue et al. |
| 5,268,074 A | 12/1993 | Brooks et al. |
| 5,277,758 A | 1/1994 | Brooks et al. |
| 5,284,610 A | 2/1994 | Tai |
| 5,285,973 A | 2/1994 | Goforth et al. |
| 5,298,102 A | 3/1994 | Pohl |
| 5,331,087 A | 7/1994 | Menges |
| 5,350,370 A | 9/1994 | Jackson et al. |
| 5,351,895 A | 10/1994 | Brooks et al. |
| 5,366,790 A | 11/1994 | Liebel |
| 5,372,878 A | 12/1994 | Saito |
| 5,374,474 A * | 12/1994 | Pratt et al. .................. 428/220 |
| 5,380,180 A | 1/1995 | Lamb, Sr. |
| 5,406,768 A | 4/1995 | Giuseppe et al. |
| 5,421,205 A | 6/1995 | Pohl |
| 5,432,000 A | 7/1995 | Young, Sr. et al. |
| 5,437,766 A | 8/1995 | Van Phan et al. |
| 5,439,542 A | 8/1995 | Liebel |
| 5,439,749 A | 8/1995 | Klasell et al. |
| 5,441,801 A | 8/1995 | Deaner et al. |
| 5,480,602 A | 1/1996 | Nagaich |
| 5,486,553 A | 1/1996 | Deaner et al. |
| 5,497,594 A | 3/1996 | Giuseppe et al. |
| 5,498,478 A | 3/1996 | Hansen et al. |
| 5,516,472 A | 5/1996 | Laver |
| 5,516,585 A | 5/1996 | Young, Sr. et al. |
| 5,518,677 A | 5/1996 | Deaner et al. |
| 5,539,027 A | 7/1996 | Deaner et al. |
| 5,540,244 A | 7/1996 | Brooks et al. |
| 5,543,205 A | 8/1996 | Liebel |
| 5,547,745 A | 8/1996 | Hansen et al. |
| 5,558,933 A | 9/1996 | Anthony |
| 5,571,618 A | 11/1996 | Hansen et al. |
| 5,574,094 A | 11/1996 | Malucelli et al. |
| 5,582,682 A | 12/1996 | Ferretti |
| 5,582,847 A | 12/1996 | Peterson et al. |
| 5,585,155 A | 12/1996 | Heikkila et al. |
| 5,614,570 A | 3/1997 | Hansen et al. |
| 5,643,359 A | 7/1997 | Soroushian et al. |
| 5,643,635 A | 7/1997 | Ahn et al. |
| 5,663,216 A | 9/1997 | Tomka |
| 5,695,874 A | 12/1997 | Deaner et al. |
| 5,746,958 A | 5/1998 | Gustafsson et al. |
| 5,759,680 A | 6/1998 | Brooks et al. |
| 5,767,177 A | 6/1998 | Omente et al. |
| 5,773,138 A | 6/1998 | Seethamraju et al. |
| 5,791,262 A | 8/1998 | Knight et al. |
| 5,819,491 A | 10/1998 | Davis |
| 5,824,246 A | 10/1998 | Reetz |
| 5,827,607 A | 10/1998 | Deaner et al. |
| 5,851,469 A | 12/1998 | Muller et al. |
| 5,871,161 A | 2/1999 | Nishibori |
| 5,876,641 A | 3/1999 | LeClair et al. |
| 5,882,564 A | 3/1999 | Puppin |

| | | | |
|---|---|---|---|
| 5,932,334 A | 8/1999 | Deaner et al. | |
| 5,948,505 A | 9/1999 | Puppin | |
| 5,948,524 A | 9/1999 | Seethamraju et al. | |
| 5,952,105 A | 9/1999 | Medoff et al. | |
| 5,973,035 A | 10/1999 | Medoff et al. | |
| 5,981,067 A | 11/1999 | Seethamraju et al. | |
| 5,985,429 A | 11/1999 | Plummer et al. | |
| 6,004,668 A | 12/1999 | Deaner et al. | |
| 6,007,656 A | 12/1999 | Heikkila et al. | |
| 6,015,611 A | 1/2000 | Deaner et al. | |
| 6,015,612 A | 1/2000 | Deaner et al. | |
| 6,054,207 A | 4/2000 | Finley | |
| 6,106,944 A | 8/2000 | Heikkila et al. | |
| 6,122,877 A | 9/2000 | Hendrickson et al. | |
| 6,207,729 B1 | 3/2001 | Medoff et al. | |
| 6,210,792 B1 | 4/2001 | Seethamraju et al. | |
| 6,258,876 B1 | 7/2001 | Medoff et al. | |
| 6,270,883 B1 | 8/2001 | Sears et al. | |
| 6,270,893 B1 | 8/2001 | Young, Sr. et al. | |
| 6,346,160 B1 | 2/2002 | Puppin | |
| 6,357,197 B1 | 3/2002 | Serino et al. | |
| 6,420,626 B1 | 7/2002 | Erspamer et al. | |
| 6,425,979 B1 | 7/2002 | Hansen et al. | |
| 6,448,307 B1 | 9/2002 | Medoff et al. | |
| 6,521,087 B1 | 2/2003 | Hansen et al. | |
| 6,620,503 B1 | 9/2003 | Qin et al. | |
| 6,670,035 B1 | 12/2003 | Pittman et al. | |
| 6,692,825 B1 | 2/2004 | Qin et al. | |
| 6,730,249 B1 | 5/2004 | Sears et al. | |
| 6,743,507 B1 | 6/2004 | Barlow et al. | |
| 6,824,729 B1 | 11/2004 | Oin et al. | |
| 6,855,182 B1 | 2/2005 | Sears | |
| 2002/0010229 A1 | 1/2002 | Medoff et al. | |
| 2002/0019614 A1 | 2/2002 | Woon et al. | |
| 2003/0032702 A1 | 2/2003 | Medoff et al. | |
| 2003/0121380 A1 | 7/2003 | Cowell et al. | |
| 2003/0125688 A1 | 7/2003 | Keane et al. | |
| 2003/0187102 A1 | 10/2003 | Medoff et al. | |

FOREIGN PATENT DOCUMENTS

| | | |
|---|---|---|
| AU | B-47811/90 | 1/1989 |
| DE | 43 31 747 | 3/1995 |
| DE | 43 31 747 A1 | 3/1995 |
| EP | 0 161 766 | 11/1985 |
| EP | 0 161 766 A1 | 11/1985 |
| EP | 0 330 729 A1 | 9/1988 |
| EP | 0 409 525 A2 | 7/1990 |
| GB | 2104903 | 1/1983 |
| GB | 2171953 | 9/1986 |
| JP | 60-168611 | 2/1985 |
| JP | 61-243805 | 10/1986 |
| JP | 61-273805 | 2/1988 |
| JP | 63-033441 | 2/1988 |
| JP | 63-033442 | 2/1988 |
| JP | 63-033448 | 2/1988 |
| JP | 63-0334401 | 2/1988 |
| WO | WO 92/07022 | 4/1992 |
| WO | WO 95/08954 | 3/1995 |
| WO | WO 96/13468 | 5/1996 |
| WO | WO 96/13551 | 5/1996 |
| WO | WO 97/06942 | 2/1997 |
| WO | WO 97/18173 | 5/1997 |
| WO | WO 99/11453 | 3/1999 |
| WO | WO 99/23138 | 5/1999 |
| WO | WO 00/29183 | 5/2000 |
| WO | WO 00/34567 | 6/2000 |
| WO | WO 02/14039 A1 | 2/2002 |

OTHER PUBLICATIONS

Abstract of (Doctorate) Dissertation Abstract Int. B1988, 58(9), 4962 (Published in Sep. 1997), in Chemical Abstracts 128:128805.

Abstract of JP 09213296, filed Feb. 5, 1996, in Chemical Abstracts 127:223004.

Supplementary European Search Report, EP 03 71 1572, Feb. 28, 2005.

Kokta et al., "Use of Wood Fibers in Thermoplastic Composites", Polymer Composites, Oct. 1983, vol. 4, No. 4, pp. 229-232.

Yam et al., "Composites From Compounding Wood Fibers With Recycled High Density Polyethylene", Polymer Engineering and Science, Mid-Jun. 1990, vol. 30, No. 11, pp. 693-699.

Zadorecki et al., "Future Prospects for Wood Cellulose as Reinforcement in Organic Polymer Composites", Polymer Composites, Apr. 1989, vol. 10, No. 2, pp. 69-77.

Woodhams et al., "Wood Fibers as Reinforcing Fillers for Polyolefins", Polymer Engineering and Science, Oct. 1984, vol. 24, No. 15, pp. 1166-1171.

Maldas et al., "Composites of Polyvinyl Chloride-Wood Fibers: IV. Effect of the Nature of Fibers", Journal of Vinyl Technology, Jun. 1989, vol. 11, No. 2, pp. 90-98.

Raj et al., "Use of Wood Fibers as Filler in Common Thermoplastic Studies on Mechanical Properties", Science and Engineering of Composite Materials, vol. 1, No. 3, 1989, pp. 85-98.

Kokta et al. "Use of Grafted Wood Fibers in Thermoplastic Composites V. Polystyrene", pp. 85-96.

Klason et al., "The Efficiency of Cellulosic Fillers in Common Thermoplastics. Part I. Filling Without Processing Aids or Coupling Agents", International Journal of Polymeric Materials, Mar. 1984, pp. 159-187.

Dalvag et al., "The Efficiency of Cellulosic Fillers in Common Thermoplastics. Part II. Filling with Process Aids and Coupling Agents", International Journal of Polymeric Materials, 1985, vol. 11, pp. 9-38.

Rogalski et al., "Poly(Vinyl-Chloride) Wood Fiber Composites", Antec '87, pp. 1436-1441.

Raj et al., "Use of Wood Fibers in Thermoplastics. VII. The Effect of Coupling Agents in Polyethylene-Wood Fiber Composites", Journal of Applied Polymer Science, vol. 37, (1989), pp. 1089-1103.

Kokta et al., "Composites of Polyvinyl Chloride-Wood Fibers. I. Effects of Isocyanate as a Bonding Agent", Polym. Plast. Technol. Eng. 29(1&2), 1990, pp. 87-118.

Kokta et al., "Composites of Polyvinyl Chloride-Wood Fibers. III. Effect of Silane as Coupling Agent", Journal of Vinyl Technology, Sep. 1990, vol. 12, No. 3, pp. 146-153.

Kokta et al., "Composites of Poly(Vinyl Chloride) and Wood Fibers. Part II: Effect of Chemical Treatment", Polymer Composites, Apr. 1990, vol. 11, No. 2, pp. 84-89.

* cited by examiner

FIGURE

CELLULOSIC AND LIGNOCELLULOSIC MATERIALS AND COMPOSITIONS AND COMPOSITES MADE THEREFROM

CROSS-REFERENCE TO RELATED APPLICATIONS

This application is a divisional of U.S. patent application Ser. No. 09/772,593, filed Jan. 30, 2001, which is a continuation-in-part of U.S. patent application Ser. No. 09/337,580, filed Jun. 22, 1999 now U.S. Pat. No. 6,207,729, which is a continuation in part of U.S. patent application Ser. No. 08/961,863, filed Oct. 31, 1997, now issued as U.S. Pat. No. 5,973,035; is a continuation-in-part of U.S. patent application Ser. No. 09/338,209, filed Jun. 22, 1999 now abandoned, which is a continuation-in-part of U.S. patent application Ser. No. 08/921,807, filed Sep. 2, 1997, now issued as U.S. Pat. No. 5,952,105; and is a continuation in part of U.S. patent application Ser. No. 09/290,031, filed Apr. 9, 1999 now U.S. Pat. No. 6,258,876, hereby incorporated by reference.

BACKGROUND OF THE INVENTION

The invention relates to texturized cellulosic or lignocellulosic materials and compositions and composites made from such texturized materials.

Cellulosic and lignocellulosic materials are produced, processed, and used in large quantities in a number of applications. Once used, these materials are usually discarded. As a result, there is an ever-increasing amount of waste cellulosic and lignocellulosic material.

SUMMARY OF THE INVENTION

In general, the invention features texturized cellulosic or lignocellulosic materials and compositions and composites made therefrom.

In one embodiment, the invention features a process for preparing a texturized fibrous material. The process involves shearing a cellulosic or lignocellulosic material having internal fibers (e.g., flax; hemp; cotton; jute; rags; finished or unfinished paper, paper products, including poly-coated paper, or byproducts of paper manufacturing such as pulp board; or synthetic cellulosic or lignocellulosic materials such as rayon), to the extent that the internal fibers are substantially exposed, resulting in texturized fibrous material. The cellulosic or lignocellulosic material can be a woven material such as a woven fabric, or a non-woven material such as paper or bathroom tissue. The exposed fibers of the texturized fibrous material can have a length/diameter (L/D) ratio of at least about 5 (at least about 5, 10, 25, 50, or more). For example, at least about 50% of the fibers can have L/D ratios of this magnitude.

In another embodiment, the invention features a texturized fibrous material that includes a cellulosic or lignocellulosic material having internal fibers, where the cellulosic or lignocellulosic material is sheared to the extent that the internal fibers are substantially exposed.

The texturized fibrous material can, for example, be incorporated into (e.g., associated with, blended with, adjacent to, surrounded by, or within) a structure or carrier (e.g., a netting, a membrane, a flotation device, a bag, a shell, or a biodegradable substance). Optionally, the structure or carrier may itself be made from a texturized fibrous material (e.g., a texturized fibrous material of the invention), or of a composition or composite of a texturized fibrous material.

The texturized fibrous material can have a bulk density less than about 0.5 grams per cubic centimeter, or even less than about 0.2 g/cm$^3$.

Compositions that include the texturized fibrous materials described above, together with a chemical or chemical formulation (e.g., a pharmaceutical such as an antibiotic or contraceptive, optionally with an excipient; an agricultural compound such as a fertilizer, herbicide, or pesticide; or a formulation that includes enzymes) are also within the scope of the invention, as are compositions that include the texturized fibrous materials and other liquid or solid ingredients (e.g., particulate, powdered, or granulated solids such as plant seed, foodstuffs, or bacteria).

Composites that include thermoplastic resin and the texturized fibrous materials are also contemplated. The resin can be, for example, polyethylene, polypropylene, polystyrene, polycarbonate, polybutylene, a thermoplastic polyester, a polyether, a thermoplastic polyurethane, polyvinylchloride, or a polyamide, or a combination of two or more resins.

In some cases, at least about 5% by weight (e.g., 5%, 10%, 25%, 50%, 75%, 90%, 95%, 99%, or about 100%) of the fibrous material included in the composites is texturized. The composite may include, for example, about 30% to about 70% by weight resin and about 30% to about 70% by weight texturized fibrous material, although proportions outside of these ranges may also be used. The composites can be quite strong, in some cases having a flexural strength of at least about 6,000 to 10,000 psi.

In another embodiment, the invention features a composite including a resin, such as a thermoplastic resin, and at least about 2% by weight, more preferably at least about 5% by weight, texturized cellulosic or lignocellulosic fiber. The invention also features a composite that includes polyethylene and at least about 50% by weight texturized cellulosic or lignocellulosic fiber.

The invention further features composites, including a resin and cellulosic or lignocellulosic fiber, that have flexural strengths of at least about 3,000 psi, or tensile strengths of at least about 3,000 psi.

In addition, the invention features a process for manufacturing a composite; the process includes shearing cellulosic or lignocellulosic fiber to form texturized cellulosic or lignocellulosic fiber, then combining the texturized fiber with a resin. A preferred method includes shearing the fiber with a rotary knife cutter. The invention also features a process for manufacturing a composite that includes shearing cellulosic or lignocellulosic fiber and combining the fiber with a resin.

The composites can also include inorganic additives such as calcium carbonate, graphite, asbestos, wollastonite, mica, glass, fiber glass, chalk, talc, silica, ceramic, ground construction waste, tire rubber powder, carbon fibers, or metal fibers (e.g., stainless steel or aluminum). The inorganic additives can represent about 0.5% to about 20% of the total weight of the composite.

The composite can be in the form of, for example, a pallet (e.g., an injection molded pallet), pipes, panels, decking materials, boards, housings, sheets, poles, straps, fencing, members, doors, shutters, awnings, shades, signs, frames, window casings, backboards, wallboards, flooring, tiles, railroad ties, forms, trays, tool handles, stalls, bedding, dispensers, staves, films, wraps, totes, barrels, boxes, packing materials, baskets, straps, slips, racks, casings, binders, dividers, walls, indoor and outdoor carpets, rugs, wovens, and mats, frames, bookcases, sculptures, chairs, tables, desks, art, toys, games, wharves, piers, boats, masts, pollution control products, septic tanks, automotive panels, substrates, computer housings, above- and below-ground electrical casings, furniture, picnic tables, tents, playgrounds, benches, shelters, sporting goods, beds, bedpans, thread, filament, cloth, plaques, trays, hangers, servers, pools, insulation, caskets, bookcovers, clothes, canes, crutches, and other construction, agricultural, material handling, transportation, automotive, industrial, environmental, naval, electrical, electronic, recreational, medical, textile, and consumer products. The composites can also be in the form of a fiber, filament, or film.

The terms "texturized cellulosic or lignocellulosic material" and "texturized fibrous material" as used herein, mean that the cellulosic or lignocellulosic material has been sheared to the extent that its internal fibers are substantially exposed. At least about 50%, more preferably at least about 70%, of these fibers have a length/diameter (L/D) ratio of at least 5, more preferably at least 25, or at least 50. An example of texturized cellulosic material is shown in FIG. 1.

The texturized fibrous materials of the invention have properties that render them useful for various applications. For example, the texturized fibrous materials have absorbent properties, which can be exploited, for example, for pollution control. The fibers are generally biodegradable, making them suitable, for example, for drug or chemical delivery (e.g., in the treatment of humans, animals, or in agricultural applications). The texturized fibrous materials can also be used to reinforce polymeric resins.

Those composites that include texturized fibrous material and resin are strong, lightweight, and inexpensive. The raw materials used to make the composites are available as virgin or recycled materials; for example, they may include discarded containers composed of resins, and waste cellulosic or lignocellulosic fiber.

Other features and advantages of the invention will be apparent from the following detailed description, and from the claims.

BRIEF DESCRIPTION OF THE DRAWING

FIG. 1 is a photograph of a texturized newspaper, magnified fifty times.

DETAILED DESCRIPTION OF THE INVENTION

Examples of cellulosic raw materials include paper and paper products such as newsprint, poly-coated paper, and effluent from paper manufacture; examples of lignocellulosic raw materials include wood, wood fibers, and wood-related materials, as well as materials derived from kenaf, grasses, rice hulls, bagasse, cotton, jute, other stem plants (e.g., hemp, flax, bamboo; both bast and core fibers), leaf plants (e.g., sisal, abaca), and agricultural fibers (e.g., cereal straw, corn cobs, rice hulls, and coconut hair). Aside from virgin raw materials, post-consumer, industrial (e.g., offal), and processing waste (e.g., effluent) can also be used as fiber sources.

Preparation of Texturized Fibrous Material

If scrap cellulosic or lignocellulosic materials are used, they should be clean and dry. The raw material can be texturized using any one of a number of mechanical means, or combinations thereof. One method of texturizing includes first cutting the cellulosic or lignocellulosic material into ¼- to ½-inch pieces, if necessary, using a standard cutting apparatus. Counter-rotating screw shredders and segmented rotating screw shredders such as those manufactured by Munson (Utica, N.Y.) can also be used, as can a standard document shredder as found in many offices.

The cellulosic or lignocellulosic material is then sheared with a rotary cutter, such as the one manufactured by Sprout, Waldron Companies, as described in Perry's Chem. Eng. Handbook, 6th Ed., at 8–29 (1984). Although other settings can be used, the spacing between the rotating knives and bed knives of the rotary cutter is typically set to 0.020" or less, and blade rotation is set to 750 rpm or more. The rotary cutter can be cooled to 100° C. or lower during the process, for example, using a water jacket.

The texturized material is passed through a discharge screen. Larger screens (e.g., up to 6 mm) can be used in large-scale production. The cellulosic or lignocellulosic feedstock is generally kept in contact with the blades of the rotary cutter until the fibers are pulled apart; smaller screens (e.g., 2 mm mesh) provide longer residence times and more complete texturization, but can result in lower length/diameter (L/D) aspect ratios. A vacuum drawer can be attached to the screen to maximize and maintain fiber length/diameter aspect ratio.

The texturized fibrous materials can be directly stored in sealed bags or may be dried at approximately 105° C. for 4–18 hours (e.g., until the moisture content is less than about 0.5%) immediately before use. FIG. 1 is an SEM photograph of texturized newspaper.

Alternative texturizing methods include stone grinding, mechanical ripping or tearing, and other methods whereby the material's internal fibers can be exposed (e.g., pin grinding, air attrition milling).

Uses of Texturized Fibrous Material

Texturized fibrous materials and compositions and composites of such fibers with other chemicals and chemical formulations can be prepared to take advantage of the material's properties. The materials can be used to absorb chemicals, for example, potentially absorbing many times their own weight. Thus, the materials could, for instance, be used to absorb spilled oil, or for clean-up of environmental pollution, for example, in water, in the air, or on land. Similarly, the material's absorbent properties, together with its biodegradability, also make them useful for delivery of chemicals or chemical formulations. For example, the materials can be treated with solutions of enzymes or pharmaceuticals such as antibiotics, nutrients, or contraceptives, and any necessary excipients, for drug delivery (e.g., for treatment of humans or animals, or for use as or in animal feed and/or bedding), as well as with solutions of fertilizers, herbicides, or pesticides. The materials can optionally be chemically treated to enhance a specific absorption property. For example, the materials can be treated with silanes to render them lipophilic.

Compositions including texturized materials combined with liquids or particulate, powdered, or granulated solids can also be prepared. For example, texturized materials can be blended with seeds (i.e., with or without treatment with a solution of fertilizer, pesticides, etc.), foodstuffs, or bacteria (e.g., bacteria that digest toxins). The ratio of fibrous materials to the other components of the compositions will depend on the nature of the components and readily be adjusted for a specific product application.

In some cases, it may be advantageous to associate the texturized fibrous materials, or compositions or composites of such materials, with a structure or carrier such as a netting, a membrane, a flotation device, a bag, a shell, or a biodegradable substance. Optionally, the structure of carrier may itself be made of a texturized fibrous material (e.g., a material of the invention), or a composition or composite thereof.

Composites of Texturized Fibrous Material and Resin

Texturized fibrous materials can also be combined with resins to form strong, lightweight composites. Materials that have been treated with chemicals or chemical formulations, as described above, can similarly be combined with biodegradable or non-biodegradable resins to form composites, allowing the introduction of, for example, hydrophilic substances into otherwise hydrophobic polymer matrices. Alternatively, the composites including texturized fibrous materials and resin can be treated with chemicals or chemical formulations.

The texturized cellulosic or lignocellulosic material provides the composite with strength. The composite may include from about 10% to about 90%, for example from about 30% to about 70%, of the texturized cellulosic or lignocellulosic material by weight.

The resin encapsulates the texturized cellulosic or lignocellulosic material in the composites, and helps control the shape of the composites. The resin also transfers external loads to the fibrous materials and protects the fiber from environmental and structural damage. Composites can include, for example, about 10% to about 90%, more preferably about 30% to about 70%, by weight, of the resin.

Resins are used in a variety of applications, for example, in food packaging. Food containers made of resins are typically used once, then discarded. Examples of resins that are suitably combined with texturized fibers include polyethylene (including, e.g., low density polyethylene and high density polyethylene), polypropylene, polystyrene, polycarbonate, polybutylene, thermoplastic polyesters (e.g., PET), polyethers, thermoplastic polyurethane, PVC, polyamides (e.g., nylon) and other resins. It is preferred that the resins have a low melt flow index. Preferred resins include polyethylene and polypropylene with melt flow indices of less than 3 g/10 min, and more preferably less than 1 g/10 min.

The resins can be purchased as virgin material, or obtained as waste materials, and can be purchased in pelletized or granulated form. One source of waste resin is used polyethylene milk bottles. If surface moisture is present on the pelletized or granulated resin, however, it should be dried before use.

The composites can also include coupling agents. The coupling agents help to bond the hydrophilic fibers to the hydrophobic resins. Examples of coupling agents include maleic anhydride modified polyethylenes, such those in the FUSABOND® (available from DuPont, Delaware) and POLYBOND® (available from Uniroyal Chemical, Connecticut) series. One suitable coupling agent is a maleic anhydride modified high density polyethylene such as FUSABOND® MB 100D.

The composites can also contain additives known to those in the art of compounding, such as plasticizers, lubricants, antioxidants, opacificers, heat stabilizers, colorants, flame retardants, biocides, impact modifiers, photostabilizers, and antistatic agents.

The composites can also include inorganic additives such as calcium carbonate, graphite, asbestos, wollastonite, mica, glass, fiber glass, chalk, silica, talc, ceramic, ground construction waste, tire rubber powder, carbon fibers, or metal fibers (e.g., aluminum, stainless steel). When such additives are included, they are typically present in quantities of from about 0.5% up to about 20–30% by weight. For example, submicron calcium carbonate can be added to the composites of fiber and resin to improve impact modification characteristics or to enhance composite strength.

Preparation of Compositions

Compositions containing the texturized cellulosic or lignocellulosic materials and chemicals, chemical formulations, or other solids can be prepared, for example, in various immersion, spraying, or blending apparatuses, including, but not limited to, ribbon blenders, cone blenders, double cone blenders, and Patterson-Kelly "V" blenders.

For example, a composition containing 90% by weight texturized cellulosic or lignocellulosic material and 10% by weight ammonium phosphate or sodium bicarbonate can be prepared in a cone blender to create a fire-retardant material for absorbing oil.

Preparation of Composites of Texturized Fiber and Resin

Composites of texturized fibrous material and resin can be prepared as follows. A standard rubber/plastic compounding 2-roll mill is heated to 325–400° F. The resin (usually in the form of pellets or granules) is added to the heated roll mill. After about 5 to 10 minutes, the coupling agent is added to the roll mill. After another five minutes, the texturized cellulosic or lignocellulosic material is added to the molten resin/coupling agent mixture. The texturized material is added over a period of about 10 minutes.

The composite is removed from the roll mill, cut into sheets and allowed to cool to room temperature. It is then compression molded into plaques using standard compression molding techniques.

Alternatively, a mixer, such as a Banbury internal mixer, is charged with the ingredients. The ingredients are mixed, while the temperature is maintained at less than about 190° C. The mixture can then be compression molded.

In another embodiment, the ingredients can be mixed in an extruder mixer, such as a twin-screw extruder equipped with co-rotating screws. The resin and the coupling agent are introduced at the extruder feed throat; the texturized cellulosic or lignocellulosic material is introduced about ⅓ of the way down the length of the extruder into the molten resin. The internal temperature of the extruder is maintained at less than about 190° C. At the output, the composite can be, for example, pelletized by cold strand cutting.

Alternatively, the mixture can first be prepared in a mixer, then transferred to an extruder.

In another embodiment, the composite can be formed into fibers, using fiber-forming techniques known to those in the art, or into filaments for knitting, warping, weaving, braiding, or making non-wovens. In a further embodiment, the composite can be made into a film.

Properties of the Composites of Texturized Fibrous Material and Resin

The resulting composites include a network of fibers, encapsulated within a resin matrix. The fibers form a lattice network, which provides the composite with strength. Since the cellulosic or lignocellulosic material is texturized, the amount of surface area available to bond to the resin is increased, in comparison to composites prepared with un-texturized cellulosic or lignocellulosic material. The resin binds to the surfaces of the exposed fibers, creating an intimate blend of the fiber network and the resin matrix. The intimate blending of the fibers and the resin matrix further strengthens the composites.

Uses of the Composites of Texturized Fibrous Material and Resin

The resin/fibrous material composites can be used in a number of applications. The composites are strong and light weight; they can be used, for example, as wood substitutes. The resin coating renders the composites water-resistant, so they may be used in outdoor applications. For example, the composites may be used to make pallets, which are often stored outdoors for extended periods of time, wine staves, rowboats, furniture, skis, and oars. Many other uses are contemplated, including panels, pipes, decking materials, boards, housings, sheets, poles, straps, fencing, members, doors, shutters, awnings, shades, signs, frames, window casings, backboards, wallboards, flooring, tiles, railroad ties, forms, trays, tool handles, stalls, bedding, dispensers, staves, films, wraps, totes, barrels, boxes, packing materials, baskets, straps, slips, racks, casings, binders, dividers, walls, indoor and outdoor carpets, rugs, wovens, and mats, frames, bookcases, sculptures, chairs, tables, desks, art, toys, games, wharves, piers, boats, masts, pollution control products, septic tanks, automotive panels, substrates, computer housings, above- and below-ground electrical casings, furniture, picnic tables, tents, playgrounds, benches, shelters, sporting goods, beds, bedpans, thread, filament, cloth, plaques, trays, hangers, servers, pools, insulation, caskets, bookcovers, clothes, canes, crutches, and other construction, agricultural, material handling, transportation, automotive, industrial, environmental, naval, electrical, electronic, recreational, medical, textile, and consumer products. Numerous other applications are also envisioned. The composites may also be used, for example, as the base or carcass for a veneer product. Moreover, the composites can be, for example, surface treated, grooved, milled, shaped, imprinted, textured, compressed, punched, or colored. The surface of the composites can be smooth or rough.

The following examples illustrate certain embodiments and aspects of the present invention and not to be construed as limiting the scope thereof.

EXAMPLES

Example 1

A 1500 pound skid of virgin, half-gallon juice cartons made of polycoated white kraft board was obtained from International Paper. Each carton was folded flat.

The cartons were fed into a 3 hp Flinch Baugh shredder at a rate of approximately 15 to 20 pounds per hour. The shredder was equipped with two rotary blades, each 12" in length, two fixed blades, and a 0.3" discharge screen. The gap between the rotary and fixed blades was 0.10".

The output from the shredder, consisting primarily of confetti-like pieces, about 0.1" to 0.5" in width and about 0.25" to 1" in length, was then fed into a Thomas Wiley Mill Model 2D5 rotary cutter. The rotary cutter had four rotary blades, four fixed blades, and a 2 mm discharge screen. Each blade was approximately 2" long. The blade gap was set at 0.020".

The rotary cutter sheared the confetti-like pieces across the knife edges, tearing the pieces apart and releasing a finely texturized fiber at a rate of about one pound per hour. The fiber had an average minimum L/D ratio of between five and 100 or more. The bulk density of the texturized fiber was on the order of 0.1 g/cc.

Example 2

Composites of texturized fiber and resin were prepared as follows. A standard rubber/plastic compounding 2-roll mill was heated to 325–400° F. The resin (usually in the form of pellets or granules) was added to the heated roll mill. After about 5 to 10 minutes, the resin banded on the rolls (i.e., it melted and fused on the rolls). The coupling agent was then added to the roll mill. After another five minutes, the texturized cellulosic or lignocellulosic material was added to the molten resin/coupling agent mixture. The cellulosic or lignocellulosic fiber was added over a period of about 10 minutes.

The composite was then removed from the roll mill, cut into sheets, and allowed to cool to room temperature. Batches of about 80 g each were compression molded into 6"×6"×⅛" plaques using standard compression molding techniques.

One composition contained the following ingredients:

| Composition No. 1 | |
| --- | --- |
| Ingredient | Amount (g) |
| High density polyethylene[1] | 160 |
| Old newspaper[2] | 240 |
| Coupling agent[3] | 8 |

[1]Marlex 16007
[2]Texturized using rotary cutter with 2 mm mesh
[3]FUSABOND ® 100D The plaques were machined into appropriate test specimens and tested according to the procedures outlined in the method specified. Three different specimens were tested for each property, and the mean value for each test was calculated. The properties of Composition No. 1 are as follows:

| | |
| --- | --- |
| Flexural strength ($10^3$ psi) | 9.81 (ASTM D790) |
| Flexural modulus ($10^5$ psi) | 6.27 (ASTM D790) |

A second composition contains the following ingredients:

| Composition No. 2 | |
| --- | --- |
| Ingredient | Amount (g) |
| High density polyethylene[1] | 160 |
| Old magazines[2] | 240 |
| Coupling agent[3] | 8 |

The properties of Composition No. 2 are as follows:

| | |
| --- | --- |
| Flexural strength ($10^3$ psi) | 9.06 (ASTM D790) |
| Flexural modulus ($10^5$ psi) | 6.78 (ASTM D790) |

A third composition contains the following ingredients:

| Composition No. 3 | |
| --- | --- |
| Ingredient | Amount (g) |
| HDPE[1] | 160 |
| Fiber paper[2] | 216 |
| 3.1 mm texturized kenaf | 24 |
| Coupling agent[3] | 8 |

The properties of Composition No. 3 are as follows:

| | |
|---|---|
| Flexural strength ($10^3$ psi) | 11.4 (ASTM D790) |
| Flexural modulus ($10^5$ psi) | 6.41 (ASTM D790) |

A fourth composition contains the following ingredients:

Composition No. 4

| Ingredient | Amount (g) |
|---|---|
| SUPERFLEX ™ $CaCO_3$ | 33 |
| Fiber[2,4] | 67 |
| HDPE (w/3% compatibilizer)[1,3] | 100 |

[4]Virgin polycoated milk cartons

The properties of Composition No. 4 are as follows:

| | |
|---|---|
| Flexural strength ($10^5$ psi) | 8.29 (ASTM D790) |
| Ultimate elongation (%) | <5 (ASTM D638) |
| Flexural modulus ($10^5$ psi) | 10.1 (ASTM D790) |
| Notch Izod (ft-lb/in) | 1.39 (ASTM D256-97) |

A fifth composition contains the following ingredients:

Composition No. 5

| Ingredient | Amount (parts) |
|---|---|
| SUPERFLEX ™ $CaCO_3$ | 22 |
| Fiber[2,4] | 67 |
| HDPE (w/3% compatibilizer)[1,3] | 100 |

The properties of Composition No. 5 are as follows:

| | |
|---|---|
| Flexural strength ($10^5$ psi) | 8.38 (ASTM D790) |
| Ultimate elongation (%) | <5 (ASTM D638) |
| Flexural modulus ($10^5$ psi) | 9.86 (ASTM D790) |
| Notch Izod (ft-lb/in) | 1.37 (ASTM D256-97) |

A sixth composition contains the following ingredients:

Composition No. 6

| Ingredient | Amount (parts) |
|---|---|
| ULTRAFLEX ™ $CaCO_3$ | 33 |
| Fiber[2,4] | 67 |
| HDPE/compatibilizer[1,3] | 100 |

The properties of Composition No. 6 are as follows:

| | |
|---|---|
| Flexural strength ($10^5$ psi) | 7.43 (ASTM D790) |
| Ultimate elongation (%) | <5 (ASTM D638) |
| Flexural modulus ($10^5$ psi) | 11.6 (ASTM D790) |
| Notch Izod (ft-lb/in) | 1.27 (astm D256-97) |

A seventh composition contains the following ingredients:

Composition No. 7

| Ingredient | Amount (pbw) |
|---|---|
| HDPE (w/3% compatibilizer)[3,5] | 60 |
| Kraftboard[2] | 40 |

[5]HDPE with melt-flow index <1

The properties of Composition No. 7 are as follows:

| | |
|---|---|
| Flexural Strength ($10^5$ psi) | 7.79 (ASTM D790) |
| Ultimate elongation (%) | <5 (ASTM D638) |
| Flexural Modulus ($10^5$ psi) | 7.19 (ASTM D790) | other embodiments are within the claims.

The invention claimed is:

1. A fibrous material including fibers comprising a cellulosic or lignocellulosic material, wherein said cellulosic or lignocellulosic material has been sheared to the extent that it has a bulk density less than about 0.5 g/cm3, and wherein at least about 50% of the fibers have a length/diameter ratio of at least about 5.

2. The fibrous material of claim 1, wherein said fibrous material is incorporated into a structure or carrier.

3. The fibrous material of claim 2, wherein the structure is selected from the group consisting of panels, pipes, decking materials, boards, housings, sheets, poles, straps, fencing, members, doors, shutters, awnings, shades, signs, frames, window casings, backboards, wallboards, flooring, tiles, railroad ties, forms, trays, tool handles, stalls, bedding, dispensers, staves, films, wraps, totes, barrels, boxes, packing materials, baskets, straps, slips, racks, casings, binders, dividers, walls, indoor and outdoor carpets, rugs, wovens, and mats, frames, bookcases, sculptures, chairs, tables, desks, art, toys, games, wharves, piers, boats, masts, pollution control products, septic tanks, automotive panels, substrates, computer housings, above- and below-ground electrical casings, furniture, picnic tables, tents, playgrounds, benches, shelters, sporting goods, beds, bedpans, thread, filament, cloth, placiues, trays, hangers, servers, pools, insulation, caskets, bookcovers, clothes, canes, crutches, and other construction, agricultural, material handling, transportation, automotive, industrial, environmental, naval, electrical, electronic, recreational, medical, textile, and consumer products.

4. The fibrous material of claim 1, wherein said fibrous material has a bulk density less than about 0.2 g/cm3.

5. The fibrous material of claim 1, wherein said fibrous material has a bulk density of about 0.1 g/cm3.

6. The fibrous material of claim 1, wherein said cellulosic or lignocellulosic material comprises paper or paper products.

7. The fibrous material of claim 1, wherein at least about 50% of the fibers have a length/diameter ratio of at least about 25.

8. The fibrous material of claim 1, wherein at least about 50% of the fibers have a length/diameter ratio of at least about 50.

9. The fibrous material of claim 1, wherein the cellulosic or lignocellulosic material is selected from the group consisting of flax, hemp, cotton, jute, rags, paper, paper products, and byproducts of paper manufacturing.

* * * * *

UNITED STATES PATENT AND TRADEMARK OFFICE
CERTIFICATE OF CORRECTION

| | | |
|---|---|---|
| PATENT NO. | : 7,074,918 B2 | Page 1 of 1 |
| APPLICATION NO. | : 10/615748 | |
| DATED | : July 11, 2006 | |
| INVENTOR(S) | : Marshall Medoff and Arthur P. Lagace | |

It is certified that error appears in the above-identified patent and that said Letters Patent is hereby corrected as shown below:

On the cover page, under "(*) Notice: Subject to any disclaimer, the term of this patent is extended or adjusted under 35 U.S.C. 154(b) by 28 days", insert --This patent is subject to a terminal disclaimer.--

Col. 10, line 24, replace "cm3", with --$cm^3$--.

Col. 10, line 43, replace "placiues", with --plaques--.

Col. 10, line 50, replace "cm3", with --$cm^3$--.

Col. 10, line 52, replace "cm3", with --$cm^3$--.

Signed and Sealed this

Twenty-sixth Day of June, 2007

JON W. DUDAS
*Director of the United States Patent and Trademark Office*